United States Patent [19]

Ranford

[11] Patent Number: 5,127,522
[45] Date of Patent: Jul. 7, 1992

[54] SHARPS CONTAINER WITH NOTCHED INSERT

[75] Inventor: Alan B. Ranford, St. Louis, Mo.

[73] Assignee: Sherwood Medical Company, St. Louis, Mo.

[21] Appl. No.: 561,742

[22] Filed: Aug. 2, 1990

[51] Int. Cl.[5] ............................................. B65D 83/10
[52] U.S. Cl. .................................. 206/366; 206/370; 206/363; 206/438
[58] Field of Search ............... 206/366, 365, 364, 363, 206/370, 438; 220/908

[56] References Cited

U.S. PATENT DOCUMENTS

| | | | |
|---|---|---|---|
| D. 302,291 | 7/1989 | Heubel et al. | |
| 4,375,849 | 3/1983 | Hanifl | 206/366 |
| 4,466,538 | 8/1984 | Gianni | 206/370 |
| 4,494,652 | 1/1985 | Nelson et al. | 206/370 |
| 4,576,281 | 3/1986 | Kirksey | |
| 4,667,821 | 5/1987 | Shillington | 206/366 |
| 4,738,362 | 4/1988 | Burns et al. | 206/366 |
| 4,801,013 | 1/1989 | Bruno | 206/366 |
| 4,802,579 | 2/1989 | Hall et al. | |
| 4,828,107 | 5/1989 | Spencer | 220/908 |
| 4,842,138 | 6/1989 | Sandel et al. | 206/438 |
| 4,862,573 | 9/1989 | Kelson et al. | 206/366 |
| 4,867,309 | 9/1989 | Germain | |
| 4,972,950 | 11/1990 | Shillington | 206/370 |
| 4,979,945 | 12/1990 | Wade et al. | 206/365 |
| 4,984,686 | 1/1991 | Shillington | 206/438 |

FOREIGN PATENT DOCUMENTS 2040268 1/1979 United Kingdom .

*Primary Examiner*—David T. Fidei
*Attorney, Agent, or Firm*—Montgomery W. Smith; Richard D. Allison; Curtis D. Kinghorn

[57] ABSTRACT

A disposable sharps container having an insert mounted in the secondary opening located on the top cover of the sharps container to allow for the repeated removal of needles from medical devices such that the needle hub of the needle is insertable into a secondary opening in the sharps container to allow the needle to be removed from the medical device and the medical device may be subsequently inserted into the sharps container through a primary opening which is surrounded by a plurality of flexible flaps.

15 Claims, 1 Drawing Sheet

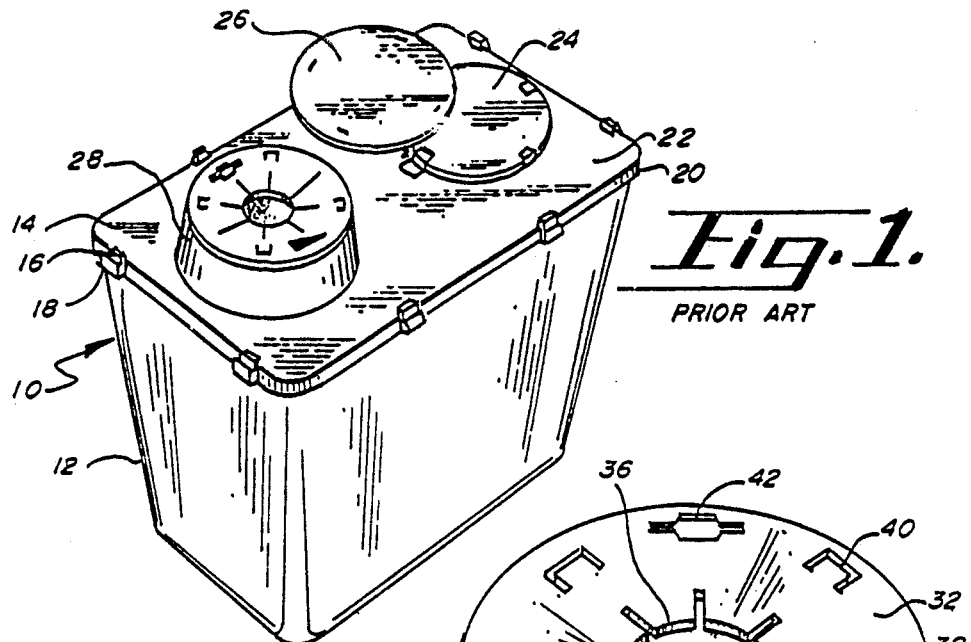
Fig. 1. PRIOR ART
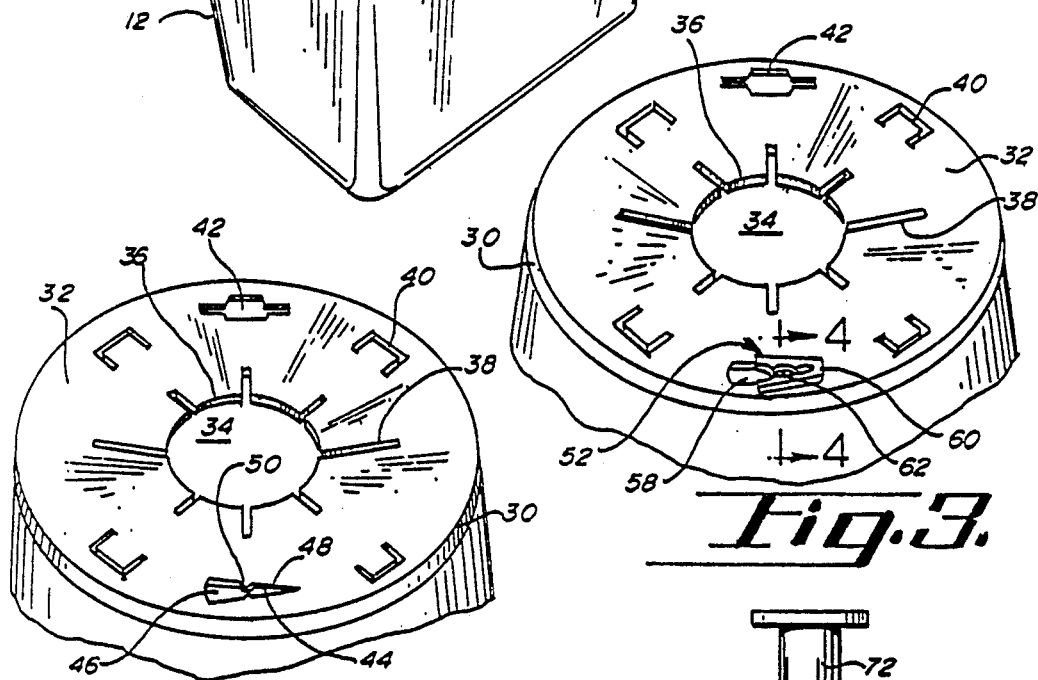
Fig. 3.
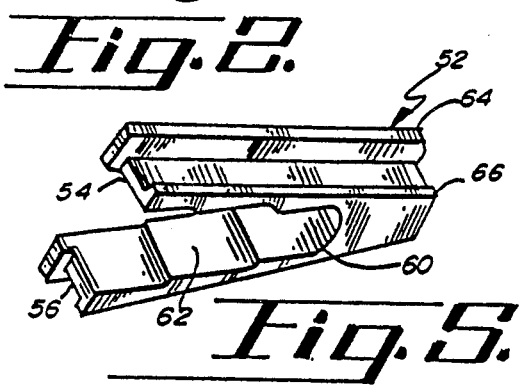
Fig. 2.
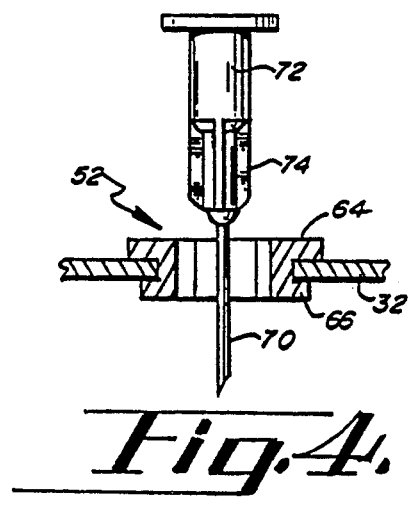
Fig. 5.
Fig. 4.

SHARPS CONTAINER WITH NOTCHED INSERT

FIELD OF THE INVENTION

The present invention relates to containers for the disposal of medical products known generally in the medical community as sharps containers and more particularly to a container having a top cover with a reinforced notched member to assist in the removal of needles from syringes or other medical devices.

BACKGROUND OF THE INVENTION

In hospitals, clinics or similar institutions, the safe disposal of used needles, syringes or other medical devices is a major concern to health care personnel. There are many currently available sharps containers which are designed to receive and safely store used medical devices. It is important that these sharps containers be readily accessible to the physician or nurse so that the medical device may be quickly and safely disposed of after use. Additionally, due to the large number of sharps containers which are used for the disposal of medical devices, it is important that the container be inexpensive and simple to use.

There are generally two types of sharps container available. The first type of sharps container has a disposable inner container with a reusable top cover and outer housing. The second type of sharps container is a completely disposable container which is intended to be disposed of once it is full. Disposable sharps containers typically have a rigid base or body section which is designed to have a sufficient volume to receive and store a large number of medical devices therein. The bottom and side walls of the body section must be constructed of a rigid material to ensure that the needles or other sharp objects do not pierce the side walls of the base section. Additionally, due to the large number of sharps containers which are used in hospitals or other large medical institutions, it is preferable to ship and store the body sections and top covers of the sharps containers in a nested condition to reduce the expenses related to the shipping and storage of a large number of sharps containers.

The top cover of the disposable sharps containers are typically constructed of a semi-rigid plastic material so that the cover will have sufficient flexibility to be snapped onto the more rigid body member. Alternately, the cover may be constructed of the same material as the body member but may be molded so that the cover is thinner and therefore, more flexible than the body member. The top cover of the sharps container typically includes multiple openings therein with various flaps or access doors associated with the openings to prevent access to the used medical devices once they are deposited in the body section of the sharps container.

As shown and described in U.S. Pat. No 4,494,652 granted to Nelson et al, and U.S. Pat. No. 4,502,606 granted to Shillington et al, one common approach to limiting access through the opening!in the resilient cover is to provide a plurality of flexible flaps which allow the user to insert used medical devices through the opening in the top cover while forming a relatively small diameter opening which will prevent access to the previously disposed of medical devices. The Nelson patent also discloses a manually operable clamp member which includes a pair of finger panels which may be squeezed together to assist the user in removing the needle from a syringe or other medical device. FIGS. 1 and 2 of the Shillington et al patent shows a pair of commonly available wrench-type structures which are formed as part of the top of the sharps container.

U.S. Pat. No. 4,375,849 granted to Hanifli discloses a small portable sharps container which is designed to receive and store used needles from medical devices such as blood collection tube holders. The cap member disclosed in this patent includes a slot member or opening with a plurality of stepped notches on one side thereof to contact the needle hub of a needle to assist in the removal of the needle from the medical device. Additionally, a movable closure lid is disclosed which rotates about the slot member to allow the user to close the opening in the cap member when the sharps container is being transported by the user.

In many of the presently available disposable sharps containers, a needle hub receiving member is formed as a molded or integral part of the cover to reduce the cost of the sharps container. Because the sharps containers are designed to hold a relatively large number of used syringes and needles therein, and because the material is semi-rigid and low cost, it is possible that the needle hub receiving member may become worn out or torn before the sharps container is full. In these situations, the needle hub receiving member will not provide adequate frictional contact with the needle hub of the used needle and the user will be unable to safely remove the needle from the medical device. The user may then risk accidental contact with the used needle by manually unthreading the needle from the medical device, or if the user is in a hurry, they may place the entire medical device in the sharps container with the needle still attached to the medical device. If the needle remains attached to the medical device, the likelihood that a subsequent user of the sharps container will accidentally contact the used needle is increased and the sharps container will also hold fewer medical devices.

One consideration in the design and manufacture of sharps containers is that the body section of the sharps container must be sufficiently rigid to prevent needles or other sharp objects from piercing the side walls of the sharps container. As a result of this need for a rigid body section, the top cover must have sufficient flexibility to allow the top cover to be locked onto the top of the body section and to allow the flaps which surround the large opening in the cover to flex as the user inserts the syringe or other used medical device into the sharps container. This need for a flexible top cover must be balanced with the need for a top cover which is sufficiently durable to withstand repeated use of the needle hub receiving notch and the manipulation of the flaps without dramatically increasing the cost of the sharps container. Finally, there is a need for the design of the sharps container to be kept as simple and convenient as possible because the user may be monitoring the patient or performing other tasks while they are disposing of the medical device. Therefore, if the sharps container is too complex or requires additional manipulation of a member on the sharps container, the likelihood that the user may accidentally contact the used needle may be increased.

The nature of this problem may be better understood with reference to the use of a specific size product. For example, a number of companies market a relatively small four quart sharps container. This sharps container has an approximate capacity of 4 quarts and it is estimated that it may hold approximately 120 used 3 cc syringes. Therefore, if the institution requires that the user remove the needle from the syringe prior to disposal, the needle notch may be used nearly 120 times before the sharps container is full. Because the top cover of many of the currently available sharps containers are manufactured of a polypropylene material and the needle hub of many currently available needles are likewise manufactured of a polypropylene material having a similar or slightly higher hardness, the needle notch may deteriorate before the sharps container is full. If the sharps container is used in a setting where a large number of blood samples are drawn, the user will typically remove the blood collection needle from the blood collection tube holder after each use and reuse the blood collection tube holder for more than one patient. In this type of situation, it is likely that needle notch will be used more often than in the situation where the sharps container is used primarily for the disposal of used needles and syringes.

SUMMARY OF THE INVENTION

It is therefore an object of the present invention to provide a simple and inexpensive sharps container which will overcome the disadvantages described above and satisfy the needs of the market place.

It is a further object of the present invention to provide a simple needle hub receiving member which will withstand repeated use and which will not wear out before the sharps container is full.

The present invention is directed to an improved top cover for a sharps container which includes a durable needle hub receiving member thereon. In the preferred form of the present invention, the openings in the top cover are raised above the generally flat surface of the top cover. The primary opening in the top cover is centrally positioned on the raised portion of the top cover and includes a plurality of flexible flaps surrounding the first opening to allow for the insertion of a syringe or other medical device therethrough. A pair of secondary openings are positioned along the periphery of the raised portion of the top cover. The secondary openings are shaped and sized to allow the user to insert the needle bearing medical device therein so that the sides of the secondary opening will mechanically contact the needle hub on the needle of the medical device. The user may then rotate the medical device until the needle is released from the medical device at which time the used needle will fall into the sharps container and the user may then reuse the medical device or dispose of the medical device through the primary opening.

As described more fully hereinafter, the present invention includes a needle hub receiving insert which is positioned in one or more of the secondary openings. The insert is preferably constructed of a material which is more rigid and durable than the cover of the sharps container and the needle hub of the used needle. In the preferred form of the present invention, the insert includes a plurality of notched areas which are oriented so that the distance between the notches gradually decreases from the larger first end of secondary opening to the smaller second end. The decreasing distance between the notches allows the present invention to be used with a variety of different sizes of needle hubs and syringes.

An advantage of the present invention is that it will not wear out before the sharps container is full.

Another advantage of the present invention is that it does not require a modification in the use of the typical sharps container.

Yet another advantage of the present invention is that it is inexpensive and does not require subsequent manipulation of the insert to remove the needle hub from the syringe.

BRIEF DESCRIPTION OF THE DRAWINGS

FIG. 1 is an elevated perspective view of a prior art sharps container;

FIG. 2 is an enlarged partial view of the raised chimney-shaped member of the sharps container shown in FIG. 1 modified for use with the insert of the present invention;

FIG. 3 is an enlarged partial view of the raised chimney-shaped member of the sharps container shown in FIG. 1 with the insert of the present invention installed thereon;

FIG. 4 is a partial cross-sectional view taken along lines 4—4 of FIG. 3 with a partial view of a commonly available needle hub and needle associated therewith; and FIG. 5 is an elevated perspective view showing the needle hub receiving insert of the present invention.

DETAILED DESCRIPTION OF THE PREFERRED EMBODIMENT

FIG. 1 is illustrative of one form of a currently available sharps container which is referred to herein generally as sharps container 10. The sharps container 10 consists generally of a body or base section 12 and a top cover 14 both of which are constructed of a polypropylene or similar material with the walls of the base section 12 being thicker and therefore more rigid than the top cover 14. A plurality of projections 16 extend upwardly from the side walls of the base section 12 in locking engagement with a plurality of similarly aligned locking members 18 on the top cover 14.

The top cover 14 includes a peripheral lip 20 which extends downwardly from the periphery of the generally flat top surface 22 of the top cover 14. A circular raised member 24 extends upwardly a slight distance from the right side of the top surface 22 to temporarily retain a cap member 26 thereon. A conically-shaped chimney member 28 extends upwardly from the top surface 22 of the top cover 14. As shown in FIG. 2, the chimney member 28 includes a peripheral rim surface 30 and a generally flat circular surface 32. The circular surface 32 includes a centrally located primary opening 34 which is surrounded by a plurality of flexible flap members 36. The flap members 36 are formed by a plurality of equally spaced and radially outwardly extending slots 38. Four equally spaced locking tabs 40 are positioned along the outer periphery of the circular surface 32. A pair of secondary openings, which are generally rectangularly shaped 42 and generally triangularly shaped 44, respectively, are opposingly positioned along the outer periphery of the circular surface 32 with both of the secondary openings 42 and 44, respectively, being positioned between a pair of locking tabs 40 and outwardly from the outer end of a slot 38. The rectangularly-shaped secondary opening 42 is a generally rectangular member having a pair of square-shaped members which intersect the ends of the rectangular member such that the secondary opening 42 includes three distinct sections having three different widths, the functions of which are described hereinafter.

As shown in FIGS. 2-5, the generally triangular-shaped secondary opening 44 of the present invention includes a semicircularly-shaped first area 46 and a triangularly-shaped second area 48 which gradually decreases in width from the semicircular area 46 to a closed second end 60. A pair of inwardly directed ribs 50 extend into the secondary opening 44 generally at the intersection of the semicircular first area 46 and the triangular second area 48. As shown in FIGS. 3-5, the needle removal notch insert 52 is constructed of a relatively rigid and durable material such as a impact modified styrene or polycarbonate which is preferably snap fit into the triangular second area 48 of the secondary opening 44. It is anticipated that in certain situations, the insert 52 may be adhesively bonded or otherwise affixed in the secondary opening 44.

As shown in FIGS. 3 and 4, the insert 52 is a generally U-shaped member having first and second legs, 54 and 56 respectively, which are spaced apart at the open first end 58 of the insert 52 and are interconnected at the closed second end 60 of the insert 52. The inner surfaces of the first and second legs 54 and 56 preferably include notched members 62 which are opposingly spaced apart on the respective legs 54 and 56 to form a decreasing width and generally stepped inner surface on the insert 52. As shown in FIG. 5, the preferred form of the present invention includes three sets of notched members 62 which are spaced apart from the opposed notch member approximately 5 mm, 4 mm and 3 mm respectively. The notched members 62 of the preferred embodiment are approximately 5 mm long. The insert 52 also includes top and bottom rims 64 and 66 respectively, which extend outwardly from the first and second legs 54 and 56 to receive the sides of the triangular second area 48 therebetween. As shown in FIG. 4, the top rim 64 extends outwardly from the top surface of the insert 52 further than the bottom rim 66 extends outwardly from the bottom surface of the insert 52 so that the insert 52 will not fall into the sharps container 10 during use, as described hereinafter.

FIG. 4 includes a partial view of a representative needle 70 and needle hub 72 which may be used on a syringe, blood collection tube holder or other medical device. As shown, the needle hub 72 includes four locking ears 74 which form a generally square outer periphery on the needle hub 72. Typically, the needles 70 manufactured by the major needle and syringe manufacturers are threadedly received on the syringe or other medical devices and include a plurality of locking ears 74 on the needle hub 72 as shown in FIG. 4. As described previously, the insert 52 of the present invention is constructed of a material which is harder than the material of the top cover 14 of the sharps container 10 and which is harder than the polypropylene needle hub 72 of the commonly used needle 70. Additionally, the insert 52 is constructed so that it will not substantially degrade if it is repeatedly used with the blood collection tube needle hubs used on many commonly available blood collection tube holders.

The insert 52 is placed in the secondary opening 44 of the circular surface 32 by slightly compressing the first and second legs 54 and 56 of the insert 52 near the open first end 58 of the insert 52 and aligning the insert 52 with the triangular second area 48 of the secondary opening 44 so that the side walls of the triangular area 48 are received between the first and second legs 54 and 56 of the insert 52 and the open first end 58 of the insert 52 is adjacent to the ribs 50. Once the insert 52 is received in the secondary opening 44 on the circular surface 32, the user may remove the needle 70 from the syringe or other medical device by inserting the needle of the medical device through the second area 48 of the secondary opening 44 until the needle hub 72 is generally aligned between the notched members 62 in the insert 52. The medical device is then moved laterally until portions of the needle hub 72 mechanically contact the notched members 62 along the inner surface of the insert 52. The user may then rotate the medical device so that the ears 74 on the needle hub 72 mechanically contact the notched members 62 and inner surface of the insert 52. Continued rotation of the medical device with respect to the insert 52 will cause the needle 70 to unthread from the medical device. Once the needle 70 is unthreaded from the medical device, the medical device and the needle 70 may be moved laterally towards the semicircular area 46 until the needle 70 falls into the sharps container 10. The user may then either reuse the medical device or deposit the used medical device through the primary opening 34 in the circular surface 32 and past the flap members 36. Once the sharps container 10 is full, the cap 26 may be locked onto the circular surface 32 by aligning the tab members (not shown) on the underside of the cap with the locking tabs 40 on the circular surface 32 to prevent the unauthorized removal of the used medical devices from the sharps container 10.

The top rim 64 on the insert 52 is particularly useful in situations where the needle 70 has been tightly threaded onto the medical device. In the past, the side walls of the secondary opening would wear out or degrade more rapidly if the user repeatedly removed needles 70 which had been strongly tightened on the medical device. With the present invention, the user may align the needle hub 72 with the top rim 64 of the insert 52 and move the medical device laterally towards the closed second end 60 of the insert 52 until the needle hub is mechanically positioned between an opposed pair of notched members 62. The user may then increase the torque which is applied as the needle 70 is removed from the medical device to overcome the locking force between the needle hub 72 and the syringe without degrading the inner surface of the insert 52. Additionally, the preferred form of the insert 52 is designed to be snap fit into the secondary opening 44 so that if the insert 52 is somehow damaged during use, a new insert 52 may be placed in the secondary opening 44 and the user may continue to use the sharps container 10 until it is full. Finally, by designing the insert 52 to function as an integral part of the sharps container 10, the user may single handedly remove the needle 70 from the medical device without having to place their other hand unacceptably close to the used needle to manipulate a clamp type member as disclosed on some prior sharps containers.

What is claimed is:

1. A disposal system for the storage of dangerous materials including needles having needle hubs removably mounted on medical devices, said system comprising:
   a base section having bottom and side walls;
   a top cover operatively associated with said base section and including a primary opening and at least one secondary opening therein, said top cover having a top surface thereon and being constructed of a first material; and an impassive insert, mounted in at least one of said secondary openings and constructed of a second material which is harder than said first material, said insert contacting and preventing the needle hub from rotating as the medical device is manually unscrewed from the needle hub whereby said second material makes said insert more resistive to deformation and premature wear due to contact with the needle hub as it is placed in said insert and thereafter unscrewed from the medical device, said insert including first and second leg members having inner and outer surfaces, said inner surfaces being opposed, wherein said outer surfaces are mounted adjacent said at least one of said secondary openings and said inner opposed surfaces include a plurality of notched members thereon, said insert also including top and bottom surfaces, said top surface including a top rim extending outwardly from said outer surface and said top rim extending adjacent at least a portion of said top surface of said cover, said bottom surface of said insert including a bottom rim extending outwardly from said outer surface and a portion of said top cover adjacent said at least one secondary opening is positioned between said top and bottom rims.

2. The disposal system of claim 1 wherein said notched members are aligned as opposed pairs of notched members which extend inwardly from said opposed inner surfaces of said first leg member and said second leg member and which are adapted to mechanically receive the needle hub of a medical device therebetween.

3. The disposal system of claim 2 wherein said pairs of notched members are spaced apart from each other a distance of between approximately 3 and 5 mm.

4. A disposal system for the receipt and storage of used medical devices therein, the disposal system comprising:
a rigid base section having bottom and side walls;
a top cover having top and bottom surfaces, said top cover being operatively associated with said base section and including a primary opening and at least one secondary opening therein wherein said primary opening receives used medical devices therethrough and at least some of said secondary openings receives used needles therethrough and wherein said top cover is constructed of a first semi-rigid material; and,
a generally V-shaped impassive insert mounted in said secondary opening so that used needles may pass therethrough, said insert including first and second leg members which are interconnected to form an open first end and a closed second end in said secondary opening such that the needle hub of a needle is insertable between said first and said second leg member through said open first end, said insert including inner and outer surfaces and top and bottom surfaces, said top and bottom surfaces including outwardly extending top and bottom rims thereon to retain at least a portion of said top cover therebetween, and wherein said insert is constructed of a second material which is harder than said first material, said insert contacting and preventing the needle hub from rotating as the medical device is manually unscrewed from the needle hub whereby said second material makes said insert more resistive to deformation and premature wear due to contact with the needle hub as it is placed in said insert and thereafter unscrewed from the medical device.

5. The disposal system of claim 4 wherein said at least one secondary opening includes an open area adjacent to said open first end of said insert which may receive a needle and needle hub therethrough.

6. The disposal system of claim 5 wherein said inner surface of said insert includes at least one pair of inwardly extending notched surfaces which extend inwardly from said first leg member and said second leg member.

7. The disposal system of claim 4 wherein said insert is insertable into said at least one secondary opening such that said top rim is positioned adjacent at least a portion of said top surface of said top cover and said bottom rim is positioned adjacent at least a portion of said bottom surface of said top cover.

8. A disposal system for the receipt and storage of used medical devices therein, the disposal system comprising:
a rigid base section having a bottom and upstanding sidewalls, said sidewalls including a plurality of projection extending from the top surface thereof;
a top cover constructed of a first semi-rigid material and having a generally flat top surface and a downwardly extending rim surface extending along the periphery thereof, said rim surface including a plurality of projections receiving members thereon to lock said top cover on said base section;
a raised and generally conically-shaped medical device received surface extending upwardly from said top cover, said receiving surface including a primary opening and at least one secondary opening therein wherein said primary opening includes a plurality of flexible flap members surrounding said primary opening and said at least one secondary opening including a first generally semi-circularly-shaped section and a second generally v-shaped second section;
an impassive insert mounted in said at least one secondary opening and including top and bottom surfaces and inner and outer surfaces, said insert including a top rim extending outwardly from said top surface and a bottom rim extending outwardly from said bottom surface such that said outer surface of said insert is adjacent said second section of said at least one secondary opening and at least a portion of said top cover is positioned between said top rim and said bottom rim, said inner surface of said insert including a plurality of inwardly directed members thereon which are oriented to receive the needle hub of a needle therebetween, and said insert being constructed of a second material which is harder than said first material, said insert contacting and preventing the needle hub from rotating as the medical device is manually unscrewed from the needle hub whereby said second material makes said insert more resistive to deformation and premature wear due to contact with the needle hub as it is placed in said insert and thereafter unscrewed from the medical device.

9. The disposal system of claim 1 wherein said insert includes first and second leg members having inner and outer surfaces, said inner surfaces being opposed, wherein said outer surfaces are mounted adjacent said at least one of said secondary openings.

10. The disposal system of claim 9 wherein said inner opposed surfaces include a plurality of notched members thereon.

11. The disposal system of claim 10 wherein said notched members are aligned as opposed pairs of notched members which extend inwardly from said opposed inner surfaces of said first leg member and said second leg member and which are adapted to mechanically receive the needle hub of a medical device therebetween.

12. The disposal system of claim 11 wherein said pairs of notched members are spaced apart from each other a distance of between approximately 3 and 5 mm.

13. The disposal system of claim 1 wherein said second material is a polycarbonate.

14. A disposal system for the storage of dangerous material including needles removable mounted on medical devices having needle hubs, said system comprising:
a base section having bottom and side walls;
a top cover operatively associated with said base section and including a primary opening and at least one secondary opening therein, said top cover having a top surface thereon and being constructed of a first material; and
an impassive insert including first and second leg members having inner and outer surfaces, said inner surfaces being opposed, wherein said outer surfaces are mounted adjacent said at least one of said secondary openings and said inner opposed surfaces include a plurality of notched members thereon, said insert mounted in at least one of said secondary openings, said insert also including top and bottom surfaces, said top surface including a top rim extending outwardly from said outer surface and said top rim extending adjacent at least a portion of said top surface of said cover, said bottom surface of said insert including a bottom rim extending outwardly from said outer surface and a portion of said top cover adjacent at least one secondary opening being positioned between said top and bottom rims, said insert constructed of a second material which is harder than said first material, said insert contacting and preventing the needle hub from rotating as the medical device is manually unscrewed from the needle hub whereby said second material makes said insert more resistive to deformation and premature wear due to contact with the needle hub as it is placed in said insert and thereafter unscrewed from the medical device.

15. In a sharps container having a base with a bottom and side walls and a top cover attached to the base, the top cover constructed of a first material and including a primary opening and at least one secondary opening, a method for improving the sharps container so that needles have a needle hub removably attached to medical devices, may be repeatedly removed from the medical devices throughout the useful life of the sharps container, comprising the step of:
mounting an impassive insert, contacting the needle hub of a medical device and constructed of a second material which is harder than the first material, in at least one of the secondary openings, said insert preventing a needle hub positioned within said insert from rotating as a medical device on which the needle hub of a needle is mounted is manually unscrewed from the needle hub and said second material preventing said insert from deforming and prematurely wearing out in response to contact with the needle hub as it is placed in said insert and thereafter unscrewed from the medical device, said insert including first and second leg members having inner and outer surfaces, said inner surfaces being opposed, wherein said outer surfaces are mounted adjacent said at least one of said secondary openings and said inner opposed surfaces include a plurality of notched members thereon, said insert also including top and bottom surfaces, said top surface including a top rim extending outwardly from said outer surface and said top rim extending adjacent at least a portion of said top surface of said cover, said bottom surface of said insert including a bottom rim extending outwardly from said outer surface and a portion of said top cover adjacent said at least one secondary opening is positioned between said top and bottom rims.

* * * * *